United States Patent [19]

Sauer et al.

[11] Patent Number: 5,212,178
[45] Date of Patent: May 18, 1993

[54] 8α-ACYLAMINO ERGOLINES AND USE AS PHARMACEUTICAL AGENTS

[75] Inventors: Gerhard Sauer; Thomas Brumby; Helmut Wachtel; Jonathan Turner; Peter-Andreas Löschmann, all of Berlin, Fed. Rep. of Germany

[73] Assignee: Schering Aktiengesellschaft, Berlin and Bergkamen, Fed. Rep. of Germany

[21] Appl. No.: 522,751

[22] Filed: May 14, 1990

[30] Foreign Application Priority Data

May 12, 1989 [DE] Fed. Rep. of Germany ....... 3915950

[51] Int. Cl.⁵ ..................... A61K 31/48; C07D 457/12
[52] U.S. Cl. ....................................... 514/288; 546/68
[58] Field of Search ........................... 546/68; 514/288

[56] References Cited

FOREIGN PATENT DOCUMENTS 3500251 7/1985 Fed. Rep. of Germany .

OTHER PUBLICATIONS

Stütz et al., "Derivate von (5R,8S,10R)-8-Amino-6-methylergolin als zentral wirksame dopaminerge Stimulantien," Eur. J. Med. Chem.—Chim. Ther., vol. 17, No. 6, 198, pp. 537-541 (CA 90:1983135) (1982).

Primary Examiner—Robert W. Ramsuer
Attorney, Agent, or Firm—Millen, White, Zelano & Branigan

[57] ABSTRACT

8α-acylamino ergolines are useful dopamine agonists.

12 Claims, No Drawings

8α-ACYLAMINO ERGOLINES AND USE AS PHARMACEUTICAL AGENTS

BACKGROUND OF THE INVENTION

The invention relates to 8α-acylaminoergolines, their production and use as pharmaceutical agents, and intermediate compounds for the production of 8α-acylaminoergolines.

8α-acylaminoergolines described in DOS 35 00 251 show prolactin secretion inhibitory effect. If long-chain alkyl radicals are present in the 6-position, they especially inhibit the secretion of the luteinizing hormone. 8α-diethyl-urea ad thiourea ergoline derivatives, which have a long-chain hydrocarbon radical in the 6-position, are described in EP-A-351 352. The 8α-acylaminoergoline derivatives substituted in the 6-position with a long-chain hydrocarbon radical show, in comparison with the 6-methyl derivatives, a reduced apomorphine antagonistic activity and increased dopamine agonistic activity. At the same time, the metabolic stability of the compound is maintained or improved.

SUMMARY OF THE INVENTION

The invention relates to compounds of Formula I

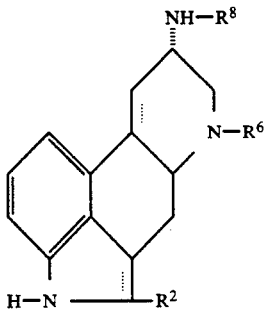

in which

C ... C each independently is a single or double bond, $R^2$ is optionally substituted $C_{1-7}$ alkyl, $C_{2-7}$ alkenyl, $CH_2-O-C_{1-4}$ alkyl or $CH_2-S-C-_{1-4}$ alkyl, $R^6$ is $C_{2-6}$ alkyl, $C_{3-6}$ alkenyl or $C_{3-5}$ cycloalkyl-$C_{1-2}$ alkyl ad $R^8$ is $-CXR^3$ or $-SO_2R^5$, in which $R^3$ is hydrogen, optionally substituted $C_{1-6}$ alkyl, S—$C_{1-6}$ alkyl, $-O-(CH_2)_n-N(CH_3)_2$ or $NR^9R^{10}$, X is oxygen or sulfur ad $R^5$ means $CH_3$ or an amino group optionally monosubstituted for disubstituted with $C_{1-4}$ alkyl, in which $R^9$ and $R^{10}$ is each independently hydrogen, $C_{1-4}$ alkyl, $C_{3-4}$ alkenyl, $-(CH_2)_nN(CH_3)_2$, $CH_2CF_3$ or together with the nitrogen atom form a 5-6 member, saturated or unsaturated heterocycle, which can be interrupted by one to two other heteroatoms, and n=1, 2, 3, or 4, as well as their acid additions salts; and $C_2 \ldots C_3$ is a single bond, if $R^2$ is methyl and $R^8$ is CO—$C_{1-6}$ alkyl ad $R^8$ does not mean CXN ($C_2H_5$)$_2$.

All alkyl groups can be straight-chain or branched alkyl radicals, for example, methyl, ethyl, n-propyl, isopropyl, n-butyl, isobutyl, sec-butyl, tert-butyl, pentyl, hexyl, heptyl, 2,2-dimethylpropyl, 2-methylbutyl, 3-methylbutyl, 1-ethylbutyl, isopentyl, isoheptyl, 1-methyl-1-ethylpropyl, and the like.

Alkyl radicals $R^2$ can be substituted, especially in the 1-position, with 1-3 of hydroxy, $C_{1-4}$-alkoxy, $C_{2-5}$-acyloxy (e.g., alkanoyloxy), or a group corresponding to the formula—$C(OR')R''R'''$, in which $R''$ and $R'''$ each independently mean hydrogen or alkyl radicals with a maximum of 6 carbon atoms ad $R'$ especially is hydrogen or acetyl or an S—$C_{1-4}$-alkyl group. Suitable acyl groups are derived from aliphatic carboxylic acids such as, for example, acetic acid, propionic acid, butyric acid, caproic acid, and trimethylacetic acid.

If $R^2$ or $R^6$ mean an alkenyl radical, the latter preferably contains only one double bond, and the double bond in radical $R^6$ cannot be adjacent to the nitrogen atom. Suitable as alkenyl radicals, for example, are: vinyl, 1-propenyl, 2-propenyl, 1-methyl-2-propenyl, 1-butenyl, methallyl, allyl, etc.

If $R^6$ means a cycloalkyl-alkyl group, for example, cyclopropylmethyl, cyclopropylethyl, cyclobutylethyl, cyclopentylmethyl, cyclopentylethyl are included.

Alkyl radical $R^3$ can be singly or doubly substituted with hydroxy, $C_{1-4}$ alkoxy, acetyloxy or dimethylamino groups, and alkyl groups with up to 3 carbon atoms and a substituent are preferred. If $R^9$ and $R^{10}$, together with the nitrogen atom, form a saturated or unsaturated heterocycle, the latter can be interrupted by oxygen, sulfur or an NH group optionally substituted with alkyl or pheyl, or can contain 2 nitrogen atoms. For example, morpholine, thiomorpholine, piperidine, imidazolidine, piperazine, pyrrolidine, pyraxolidine, imidazole, triazole, etc., are suitable.

$C_{2-4}$ alkyl, $C_{3-4}$ alkenyl or cycloalkylalkyl with up to 5 carbon atoms can be considered as suitable embodiment forms for $R^6$ and $C_{1-4}$ alkyls and $C_{2-4}$ alkenyls for $R^2$.

The compounds of Formula I can occur as E or Z isomers or, if a chiral center is present in radical $R^2$, as diastereomers and as their mixtures. Both the individual isomers per se and the isomer mixtures are included in this invention. The physiologically compatible acid addition salts can be derived from known inorganic and organic acids, such as, for example, hydrochloric acid, sulfuric acid, hydrobromic acid, citric acid, maleic acid, fumaric acid, tartaric acid, etc.

The compounds of Formula I, such as, N-(2-methyl-6-n-propyl-8-alpha-ergolinyl)-2-methyl thiopropionic acid amide, as well as their acid addition salts, especially central dopaminergic effectiveness and, therefore, can be used as pharmaceutical agents. Since they are especially distinguished by dopamine agonistic action, without α-adrenergic effects being noticeable, the compounds according to the invention are especially suitable for treatment of dopamine deficiency conditions in living beings (e.g., mammals, including humans) and especially of Parkinson's Disease.

For use of the compounds according to the invention as pharmaceutical agents, they can be produced in the form of a pharmaceutical preparation which, besides the active ingredient, contain pharmaceutical, organic, or inorganic inert vehicles, such as, for example, water, gelatin, gum arabic, lactose, starch, magnesium stearate, talc, vegetable oils, polyalkylene glycols, etc., suitable for enteral or parenteral application. The pharmaceutical preparations can be present in solid form, for example, as tablets, dragees, suppositories, capsules, or in liquid form, for example, as solutions, suspensions, or emulsions. Optionally, they further contain auxiliary agents such as preservatives, stabilizing agents, wetting agents, or emulsifiers, salts for changing the osmotic pressure, or buffers.

All compounds of this invention for treatment of Parkinson's Disease can be administered by any conventional route, e.g., parenterally or orally. A suitable dosage range is 0.00001-0.1 mg/kg/day, especially 0.001-0.1 mg/kg/day. Typically, unit dosages are 0.001-10 mg/dosage unit in a physiologically acceptable carrier. In general, they can be administered analogously to the administration of the known agent bromocryptine. Particular levels of activity and, correspondingly, more precise details of administration can be routinely determined for any given compound in conjunction with a standard pharmaceutical test such as that of Horowski et al., below.

The dopamine agonistic action was determined according to Horowski, R. and Wachtel, H. Eur. J. Pharmaz. col. 36: 373-383, 1976. One hour after i.p. pretreatment with test substance or vehicle, the presence of behavior stereotypes on rats (masticatory, licking, or gnawing movements) was determined for 2 minutes (60th-62nd min. p.i.). Animals which during the 2-minute interval showed masticatory, licking, or gnawing movements were considered as stereotypes.

The results are presented in Table 1.

Table 1

Stereotype-releasing effectiveness on rats 1 hour after i.p. pretreatment. Effective doses (ED$_{50}$) with 95% confidence limit were determined with the help of probit analysis, n=number of animals:

TABLE 1

| Stereotype-releasing effectiveness on rats 1 hour after i.p. pretreatment. Effective doses (ED$_{50}$) with 95% confidence limit were determined with the help of probit analysis, n = number of animals: | | | |
|---|---|---|---|
| | | Effectiveness | |
| Compound | n | ED$_{50}$ | 95% Confidence Limit |
| A | 8 | 0.080 | 0.010-0.170 |
| B | 8 | 0.050 | 0.034-0.079 |

A = N-(2-methyl-6-n-propyl-8α-ergolinyl)-dithiocarbamic acid methyl ester
B = N-(2-methyl-6-n-propyl-8α-ergolinyl)-thioformamide The production of the compounds according to the invention of Formula I can be performed according to methods known in the art.

For example, the compounds of formula 1 can be attained by a) a compound of formula II

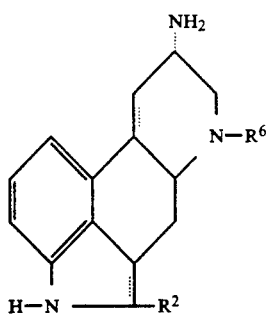

in which R$^2$ and R$^6$ have the above meaning, being acylated with an acid or its functional derivative, b) a compound of formula II and a compound of formula III

$$R^9-N=C=X \qquad III$$

in which R$^9$ and X have the above meaning, but R$^9$ cannot be hydrogen, being reacted to form a compound with R$^8$ meaning —CX—NHR$^9$, c) a compound of formula IV

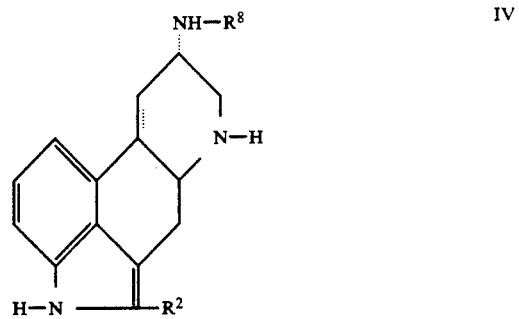

in which R$^2$ and R$^8$ have the above meaning, being alkylated or alkenylated d) a compound of formula V

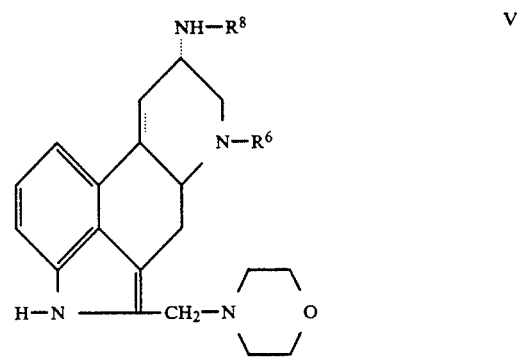

in which R$^6$ and R$^8$ have the above meaning, being substituted in the 2 position e) a compound of formula VI

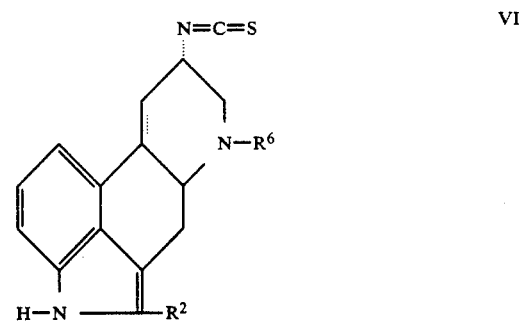

in which R$^2$ ad R$^6$ have the above-named meaning, being converted with a nucleophile to compounds of formula I with R$^3$=—S—C$_{1-6}$ alkyl, —O—(CH$_2$-)$_n$—N(CH$_3$)$_2$ or NR$^9$ R$^{10}$ in which R$^9$, R$^{10}$ and n have the above-named meaning and optionally then a C...C single bond being oxidized or a C...C double bond being reduced or a carbonyl group being thiolated or forming the acid addition salts.

The acylation of the compounds of formula I according to process a) can be performed in the usual way. Thus, free acid R$^8$OH or its reactive derivatives such as halides or anhydrides can be reacted with the amine of formula II optionally in the presence of a base in a suitable inert solvent at temperatures from room temperature to the boiling temperature of the solution mixture. Suitable as solvents are ethers such as tetrahydrofuran, dioxane, chlorinated hdyrocarbons such as dichloromethane or aprotic solvents such as DMF. In the use of an anhydride for acylation, also excess anhydride can be used as solvent. The formulaiton is suitably performed with a mixed anhydride of acetic acid and formic acid. Suitable as bases are, for example, triethylamine, Huenigh bases or 2,6-lutidine or the acylation is performed in pyridine as solvent. The production of urea and thiourea derivatives can take place, for example, by reactive imidazolides, which are obtained from N,N-carbonyldiimidazole or N,N-thiocarboyldiimidazole and primary ad second amines $R^9R^{10}HN$. Also urea derivatives can be also prepared by reaction with carbamoyl- chlorides $R^9R^{10}NCO$ Cl.

The addition of amines on isocyanates or isothiocyanates according to process b) can take place according to the method described in EP-82 808, by the reaction being performed. For example, in an inert solvent such as hydrocarbons, chlorinated hydrocarbons, ethers or esters, for example, in hexane, toluene dichloromethane, diethyl ether, ethyl acetate, etc. at room temperature or elevated temperature.

The introduction of substituents in the 8 or 2 position can take place before or after the acylation in the 8 position.

Substitution in the 8 position according to process c) can be performed, for example according to A. Cerny et al. Coll. Czech. Comm. 49, 2828 (1984) or according to the process described in EP-21 200, by the 6H compound of formula IV being reacted with the corresponding $R^6$ halides (bromides, chlorides, iodides). The reaction suitably takes place in an inert solvent such as dimethyl sulfoxide, dimethylformamide, acetonitrile or nitromethane in the presence of bases such as alkali hydroxides or carbonates.

The introduction of substituents $R^2$ can take place, for example, according to the processes described in EP-A-351 352. Here the Mannich base of formula V or its quaternary salt can be nucleophilically substituted or introduced by the 2-aldehyde derivative as intermediate compound of desired substituent $R^2$. The nucleophilic exchange takes place optionally after quaternization of the Mannich base in a polar protic or aprotic solvent such as alcohols, ethers or chlorinated hydrocarhons at room temperature or elevated temperature, and alcoholates or thiolates can be used as nucleophilic anions, which optionally can then be converted into the $CH_2$ OH group. For the production of the -methyl derivative, the quaternary salt of formula V in polar solvents such as alcohols can be reduced with sodium borohydride.

The oxidation to a 2-CHO compound can take place analogously to the process described in R.A. Jones and al. Synthetic Communications 16, 1799 (108G) with manganese dioxide or tert-butyl hypochlorite in inert solvents at room temperature. The conversion of the 2-formyl compounds to compounds of formula I, in which R means an alkenyl radical, can take place in a Wittig reaction, as, for example, with alkyl triphenylphosphonium halide in polar solvents such as cyclic and acyclic ethers, chlorinated hydrocarbons, dimethylformamide or dimethyl sulfoxide at temperatures of −50° C. to the boiling temperature of the reaction mixture, and strong bases such as alkali alcoholates, lithium organyl etc., are added for the production of the ylene.

The preparation of substituents $R^2$ hydroxylated in the 1 position can take place for example by reaction of aldehydes and ketones with Grignard compounds or lithium organyls. The Grignardization can take place with the usual Grignard reagents such as alkyl magnesium halides in an aprotic solvent such as cyclic and acyclic ethers at low temperatures (−70° C. to 0° C). The reaction with alkyl lithium takes place under analogous conditions.

The acylation of a hydroxyl group can take place according to the usual methods such as by reaction with acid anhydrides or acid chlorides.

If substituent $R^2$ contains a hydroxyl group, the latter for example, can reduced by reaction with Na $BH_4$ in glacial acetic acid to the corresponding 2-alkyl derivative or oxidized with magnesium dioxide to the ketone or dehydrated with the introduction of a double bond. If substituent $R^2$ contains a double bond, the latter, ior example, can be catalytically reduced. The introduction of substituent $R^2$ —C(OH)R"R"', can take place, as described above by the reaction of the ketone with Grignard compounds or lithium organyls.

If the compounds of formula I are prepared according to process e). the reaction conditions mentioned under process variant b) are suitable for the reaction. Alcohols, primary and secondary amines and mercaptans of formula H-RS can be used as nucleophiles, and $R^3$ means —S—$C_{1-6}$ alkyl, —O—$(CH_2)_n$—$N(CH_3)_2$ or $NR^9R^{10}$.

The optionally subsequent stereoselective hydrogenation of the 2,3-double bond can take place, for example, according to the process described in EP-A-286 575 in the presence of an acid with organylsilanes or with hydrogen/noble metal catalysts.

If optionally the introduction of the $C_2$-$C_3$ double bond is to be performed, the latter can take place, for example, according the process described in EP-A-190534 with tert-butyl hypochlorite or with $MnO_2$ according to EP-A-118840.

The conversion of the amides and urea derivatives into the thioamides and thiourea derivatives can take place, for example, according to the process described in EP-A-217 730 by reaction with phosphorus oxychloride and a thiolation agent or with Lawesson reagent according to Fieser and Fieser Reagents for Org. Synth. IX, 49. The compounds of formula I are isolated either as free bases or in the form of their physiologically compatible acid addition salts.

For the formation of salts a compound of formula I, for example, is dissolved in a little methanol or methylene chloride and mixed with a concentrated solution of the desired acid.

The isomer mixtures can be separated according to the usual methods, such as, for example crystallization, chromatography or salt formation in the diastereomers or E/Z isomers.

The invention also comprises compounds of formula II

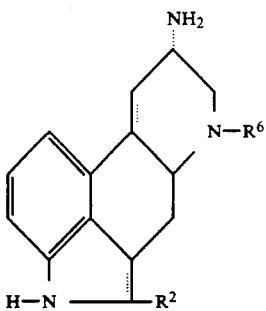

in which R² and R⁶ have the above meaning and the compounds of formula IV

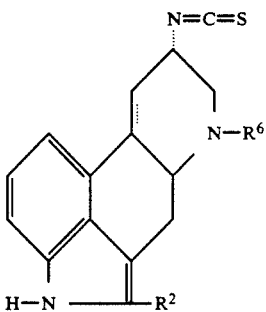

in which R² and R⁶ have the above meaning.

These compounds are valuable intermediate products for the production of pharmacologically effective compounds. The conversion of the intermediate products into the active ingredients takes place according to the above-described processes.

If the production of the initial compounds is not described herein, they are known or can be produced analogously to known compounds or processes described here using known or readily preparable starting materials.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, and of corresponding West German Application No. P 39 15 950.7, filed May 12, 1989, are hereby incorporated by reference.

STARTING COMPOUNDS

Preparation of 2,6-disubstituted 8alpha-amino-ergolines

1) A solution of 25 mmol of lithium diisopropylamide in 50 ml of tetrahydrofuran is prepared and the solution of 3.38 g of 8-n-propyl-2-vinyl-8beta-ergoline carboxylic acid methyl ester (10 mmol) in 50 ml of tetrahydrofuran is added at −30° C., it is stirred for 30 minutes at this temperature and then acidified with 10% hydrochloric acid. After heating to room temperature it is mixed with saturated bicarbonate solution, shaken out with dichloromethane and the organic phase is separated, dried and concentrated by evaporation. The residue is chromatographed on silica gel with dichloromethane/methanol. Yield of 6-n-propyl-2-vinyl-8alpha-ergoline carboxylic acid methyl ester 2.0 g (60% of theory).

Without crystallization, the 8alpha-ester is converted with hydrazine hydrate/hydrazine hydrochloride in propanol into the corresponding hydrazine nitrosated with sodium nitrite in hydrochloric acid solution to 8alpha-ergoline carboxylic acid azide and the azide is rearranged at 80° C. After cooling, it is worked up as described above and the residue is crystallized. Yield 1.33 g (45% of theory) of 8-n-propyl-2-vinyl-8alpha-ergolinyl-amine.

Other substituted ergolinyl amines can be prepared analogously. 2) 4.35 g of 1,1-diethyl-3-(2-methyl-8-n-propyl-8alpha-ergolinyl) urea (11 mmol) is suspended in 1N HCl and heated for 16 hours to 120° C. The solution is permitted to cool carefully made alkaline with ammonia solution and extracted with dichloromethane. The residue is crystallized from dichloromethane/methanol/diisopropyl ether. Yield 2.69 % (83% of theory) of 2-methyl-6-n-propyl- 8alpha-ergolinyl-amine, $[\alpha]_D = -82°$ . (0.5% in chloroform)

Analogously, the following ergolinylamines are prepared from the corresponding ergolinyl ureas or ergolinyl thioureas: 6-ethyl-2-methyl-8alpha-ergolinylamine yield 74% 6-allyl-2-methyl-8alpha-ergolinylamine yield 53% 6-cyclopropylmethyl-2-methyl-8alpha-ergolinylamine yield 59% 2,6-diethyl-8alpha-ergolinylamine yield 76% 2-ethyl-6-n-propyl-8alpha-ergolinylamine yield 81% 2-ethyl-6-allyl-8alpha-ergolinylamine yield 71% 6-ethyl-2-morphilinomethyl-8alpha-ergolinylamine yield 71% 2-morpholinomethyl-6-n-propyl-8-alpha-ergolinylamine yield 80%

3) 880 mg of 3-(9,10-didehydro-2-methyl-6-n-propyl-8alpha-ergolinyl)-1,1-diethylurea (2.3 mmol) is dissolved in 30 ml of trifluoroacetic acid and 1.48 ml of triethylsilane is added in three equal portions at intervals of 5 minutes. Then it is stirred for 60 minutes,first ice then 25% ammonia solution with cooling are added and the alkaline solution is shaken out with dichloromethane. The organic phases are dried and concentrated by evaporation. Yield after chromatography 378 mg. By crystallization from ethyl acetate/diisopropyl ether, 106 mg of the 2,3-dihydro derivative can be obtained, $[\alpha]_D = +204°$ (0.5% in chloroform).

271 mg of the crude product is heated in 40 ml of 4N HCl for 16 hours to 110° C. After cooling, it is mixed with ice, made alkaline with ammonia and shaken out from dichloromethane. The crude product is crystallized from ethyl acetate/diisopropyl ether. Yield 46 mg (23of theory) of 9,10-didehydro-2,3beta-dihydro-2beta-methyl-6-n-propyl-8alpha-ergolinylamine, $[\alpha]_D = +81°$ C. (0.2% in chloroform).

Analogously, the following 9,10-didehydro-2,3beta-dihydro 8alpha-ergolinylamines are prepared from the corresponding 9,10-didehydro-ergolinyl ureas:

9,10-didehydro-2,3beta-dihydro-6-ethyl-2beta-methyl- 8alpha-ergolinylamine yield 31%

6-allyl-9,10-didehydro-2,3beta-dihydro-2beta methyl-8alpha-ergolinylamine yield 19% 6-cyclopropylmethyl-9,10-didehydro-2,3-dihydro-2beta-methyl-8alpha-ergolinylamine yield 32% 9,10-didehydro-2,3-beta-dihydro-2,G-diethyl-8alpha-ergolinylamine yield 41% 9,10-didehydro-2,3-didehydro-2-ethyl-6-n-propyl-8alpha-ergolinylamine yield 35% 6-allyl-9,10-didehydro- 2,3beta-dihydro-2-ethyl-8alpha-ergolinylamine yield 49% 2,3beta-dihydro-8alpha-ergolinylamines can be prepared from the corresponding ergolinyl ureas according to the same specifications. 2,3beta-dihydro-2-methyl-6-n-propyl-8alpha-ergolinylamine yield 65% 2,3beta-didehydro-6-ethyl-2-methyl-8alpha-ergolinylamine yield 73% 6-allyl-2,3-beta-dihydro-2-methyl-8alpha-ergolinylamine yield 63% 2,3-dihydro-2-ethyl-6-n-propyl-8-alpha-ergolinylamine yield 78%

EXAMPLE 1

(Dimethylamino)-(2-methyl-6-n-propyl-8alpha-ergolinylamino)sulfone 30 ml of dichloromethane, 10 ml of 2,6-lutidine and 1 ml of dimethylaminosulfonic acid chloride (10 mmol) are mixed at room temperature. The suspension of 300 ml of 2-methyl-6-n-propyl-8alpha-ergolinylamine (1.06 mmol in 30 ml of dichloromethane is added to it and stirred for 1G hours at room temperature and then 2 hours at 50° C. The reaction solution is shaken three times with 200 ml each of saturated copper sulfate solution, the organic phase is washed with water, dried and concentrated by evaporation, finally in a high vacuum. The crude product is chromatographed on silica gel with dichloromethane/methanol and crystallized from ethyl acetate/diisopropyl ether/hexane. Yield 73 mg (17% of theory), $[\alpha]_D = -44.9°$ (0.5% of chloroform).

Analogously, there is produced with diethylaminosulfonic acid chloride: (diethylamino)-(2-methyl-6-n-propyl-8alpha-ergolinylamino)-sulfone. Yield 25% as tartaric acid salt, $[\alpha]_D = -34°$ (0.5% in methanol).

EXAMPLE 2

Analogously to example 1, there is prepared from 9,10-didehydro-2,3beta-dihydro-2-methyl-0-n-propyl-8alpha-ergolinylamine:

(9,10-didehydro-2,3beta dihydro-2-methyl-6-n-8alphaergoliylamino)-dimethylaminosulfone, yield 37%.

EXAMPLE 3

(9,10-didehydro-2-methyl-6-n-propyl-8alpha-ergolinyl)-dimethylamino-sulfone 390 mg of (9,10-didehydro-2,3beta-dihydro-2-methyl-6-n-propyl-8alpha-ergolinylamino)-dimethylamino-sulfone (1 mol) is dissolved in 30 ml of anhydrous tetrahydrofuran and 0.5 ml of riethylamine and the mixture is cooled to −40° C. 0.16 ml of tert-butyl hypochlorite (1.34 mmol) in 10 of anhydrous tetrahydrofuran is instilled and stirred for 30 minutes at −40° C. The mixture is poured onto ice, made alkaline with ammonia and extracted with dichloromethane. The organic phases are dried, concentrated by evaporation and the residue is chromatographed on silica gel with dichloromethane/methanol and crystallized. Yield 217 mg (56% of theory).

EXAMPLE 4

N-(2-methyl-6-n-propyl-8alpha-ergolinyl)-formamide 849 mg of 2-methyl-6-n-propyl-8alpha-ergolinylamine (3 mmol) is dissolved in 40 ml of tetrahydrofuran and 3.75 ml of a mixture of 6.15 ml of 98% formic acid, 12.5 ml of acetic anhydride and 10 ml of anhydrous tetrahydrofuran are added. After 30 minutes of stirring at room temperature, ice is added it is made alkaline with ammonia and shaken out with dichloromethane. The organic phases is dried, the solvent is evaporated and the residue is chromatographed on silica gel with ethyl acetate/methanol and crystallized from diisopropyl ether, yield 647 mg (69% of theory), $[\alpha]_D = +30°$, (0.5% in chloroform).

Analogously there are prepared:

from 2,3beta-dihydro-2-methyl6n-propyl-8alpha-ergolinylamine the N-2,3beta-dihydro-2-methyl-6-n-propyl-8alpha-ergolinylamine)-formamide, yield 61% from 2-ethyl-6n-propyl-8alpha-ergolinylamine the N-(2ethyl-6-n-propyl-8alpha-ergolinyl)-formamide, yield 63% from 9,10-didehydro-2,3beta-dihydro-2-methyl-6-n-propyl8alpha-ergolinylamine the N-(9,10-didehydro-2,3-beta-dihydro-2-methyl-6-n-propyl-8alpha-ergolinyl)-formamide, yield 73% from 6-allyl-9,10-didehydro-2,3-beta-dihydro-2-methyl8alpha-ergolinylamine the N-(6-allyl-9,10-didehydro-2,3betadihydro-2-methyl-8alpha-ergolinyl)-formamide yield 54% from 9,10-didehydro-2,3beta-dihydro-2-ethyl-6-n-propyl8alpha-ergolinylamine the N-(9,10-didehydro-2,3-beta-dihydro-2-ethyl-6n-propyl-8alpha-ergolinyl)-formamide, yield 71%

EXAMPLE 5

Analogously to example 3, there are obtained:

from N-(9,10-didehydro-2,3-beta-dihydro-2-methyl-6-n-propyl8alpha-ergolinyl)-formamide by oxidation with tert-butyl hypochlorite the N-(9,10-didehydro-2-methyl-6-n-propyl-8alpha-ergolinyl)-formamide, yield 66% from N-(6-allyl-9,10-didehydro-2,3-beta-dihydro-2-methyl8alpha-ergolinyl)-formamide the N-(6-allyl-9,10-didehydro-2-methyl-8alpha-ergolinyl)-formamide, yield 48% from N-(9,10-didehydro-2,8beta-dihydro-2-ethyl-6-n-propyl8alpha-ergolinyl)-formamide the N-(9,10-didehydro-2-ethyl-6-n-propyl-8alpha-ergolinyl)-formamide, yield 63%

EXAMPLE 6

N-(2-methyl-6-n-propyl-8alpha-ergolinyl)-methoxyacetamide 849 mg of 2-methyl6n-propyl-8alpha-ergolinylamine (3 mmol) is dissolved in 20 ml of pyridine and stirred with 2.28 ml of methoxy acetyl chloride (30 mmol) for 30 minutes at room temperature. Then it is poured onto ice, stirred for 15 minutes, make alkaline with ammonia and extracted with dichloromethane. The organic phases are dried and concentrated by evaporation. The residue is chromatographed on silica gel with ethyl acetate/methanol and crystallized from ethyl acetate. Yield 420 mg (40% of theory), $[\alpha]_D = +24°$ (0.5% in chloroform).

EXAMPLE 7

By acylation with the corresponding carboxylic acid chlorides or anhydrides, analogously to example 6, the following amides are obtained:

N-(2,3-dihydro-2-methyl6n-propyl-8alpha-ergolinyl)-methoxyacetamide, yield 63%

N-(2-methyl-6-n-propyl-8alpha-ergolinyl)-acetoxyacetamide, yield 19%, $[\alpha]_D = +27°$ (0.5% in chloroform).

N-(9,10-didehydro-2,3-dihydro-2-methyl6n-propyl-8alpha-ergolinyl)-acetoxyacetamide, yield 41%.

EXAMPLE 8

Analogously to example 3, N-(9,10-didehydro-2-methyl-6-n-propyl-8alpha-ergolinyl)-acetoxyacetamide is obtained from N-(9,10-didehydro-2,3-dihydro-2-methyl-6-n-propyl-8alpha-ergolinyl)-acetoxyacetamide by oxidation with tert-butyl hypochlorite, yield 63%.

EXAMPLE 9

N-(2-methyl-6-n-propyl-8alpha-ergolinyl)-2-hydroxyacetamide 530 mg of N-(2-methyl6n-propyl-8alpha-ergolinyl)-acetoxyacetamide (1.38 mmol) is dissolved in 20 ml of methanol and 0.5 ml of KOH and stirred for 15 minutes at room temperature. Then it is mixed with ice and shaken out with dichloromethane. The organic phases are dried, concentrated by evaporation and crystallized from diisopropyl ether/hexane, yield 321 mg (63% of theory). $[\alpha]_D + 20°$ (0.5% in chloroform).

Analogously, the hydrolysis results in the following 2-hydroxyacetamide:

N-(9,10-didebydro-2-methyl-6-n-propyl-8alpha-ergolinyl)-2-hydroxyacetamide

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I

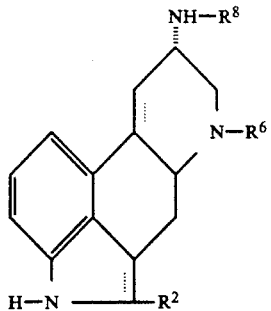

in which
CC each independently is a single or double bond;
$R^2$ is optionally substituted $C_{1-7}$-alkyl, or $C_{2-7}$-alkenyl, $CH_2$—O—$C_{1-4}$-alkyl, or $CH_2$—S—$C_{1-4}$-alkyl;
$R^6$ is $C_{2-6}$ alkyl, $C_{3-6}$-alkenyl, or $C_{3-5}$-cycloalkyl-$C_{1-2}$-alkyl;
$R^8$ is —$CXR^3$,
$R^3$ is hydrogen or optionally substituted $C_{1-6}$-alkyl;
or a pharmaceutically acceptable acid addition salt thereof.

2. A compound of claim 1, wherein $C_2$–$C_3$ is a saturated bond.
3. A compound of claim 1, wherein $C_2$–$C_3$ is an unsaturated bond.
4. A compound of claim 1, wherein $C_9$–$C_{10}$ is a saturated bond.
5. A compound of claim 1, wherein $C_9$–$C_{10}$ is an unsaturated bond.
6. A compound of claim 1, wherein $R^6$ is alkyl, alkenyl, or cycloalkylalkyl.
7. A compound of claim 1, wherein $R^6$ is $C_{2-4}$-alkyl, $C_{3-4}$-alkenyl, or cycloalkylalkyl of up to 5 total C atoms.
8. A compound of claim 1, wherein $R^2$ is alkyl or alkenyl.
9. A compound of claim 1, wherein $R^2$ is $C_{1-4}$-alkyl or $C_{2-4}$-alkenyl.
10. A composition comprising a compound of claim 1 and a pharmaceutically acceptable carrier.
11. A method of treating Parkinson's Disease comprising administering a compound of claim 1.
12. N-(2-methyl-6-n-propyl-8-alpha-ergolinyl)-2-methylthiopropiic aicd amide,
N-(2-methyl-6-n-propyl-8-alpha-ergolinyl)thioformamide each a compound of claim 1.

* * * * *

UNITED STATES PATENT AND TRADEMARK OFFICE
CERTIFICATE OF CORRECTION

PATENT NO. : 5,212,178

DATED : May 18, 1993

INVENTOR(S) : Gerhard SAUER et al.

It is certified that error appears in the above-identified patent and that said Letters Patent is hereby corrected as shown below:

Claim 12; Col. 12; Line 46.

Reads: (methylthiopropiic aicd amide.)

Should read--"methylthiopropionic acid amide.--"

Signed and Sealed this

Twenty-second Day of February, 1994

Attest:

BRUCE LEHMAN

Attesting Officer   Commissioner of Patents and Trademarks